United States Patent [19]

Cella et al.

[11] Patent Number: 4,814,466

[45] Date of Patent: Mar. 21, 1989

[54] METHOD FOR MAKING THIANTHRENE DIANHYDRIDE AND POLYIMIDES OBTAINED THEREFROM

[75] Inventors: James A. Cella, Clifton Park; Deborah A. Haitko, Schenectady, both of N.Y.

[73] Assignee: General Electric Company, Schenectady, N.Y.

[21] Appl. No.: 179,370

[22] Filed: Apr. 8, 1988

Related U.S. Application Data

[63] Continuation-in-part of Ser. No. 45,118, May 4, 1987.

[51] Int. Cl.$^4$ ............................................ C07D 339/08
[52] U.S. Cl. ........................................ 549/15; 549/17
[58] Field of Search ................................... 549/17, 15

[56] References Cited

PUBLICATIONS

Pebalk, D. V. et al., "Electron-Acceptor Properties of Aromatic Dianhydrides", Dokl. Akad. Nauk SSSR (1977) 236(6), pp. 1379–1382 (U.S.S.R.).

Pebalk, D. V., et al., "Spin Density Distribution in Anion Radicals of Aromatic Tetracarboxylic Acid Dianhydrides", Dokl. Akad. Nauk SSSR (1979) 244(5), pp. 1169–1173 (U.S.S.R.).

Primary Examiner—Harold D. Anderson
Assistant Examiner—Frederick Krass
Attorney, Agent, or Firm—William A. Teoli; James C. Davis, Jr.; James Magee, Jr.

[57] ABSTRACT

A method is provided for making 9,10-dithiaanthracene-2,3,6,7-tetracarboxylic acid dianhydride. Polyimides having improved oxidative stability also are provided which can be made intercondensing organic diamine and the aforementioned dianhydride or a dianhydride mixture.

1 Claim, No Drawings

METHOD FOR MAKING THIANTHRENE DIANHYDRIDE AND POLYIMIDES OBTAINED THEREFROM

BACKGROUND OF THE INVENTION

This application is a continuation-in-part of copending application Ser. No. 045,118, filed May 4, 1987, assigned to the same assignee as the present invention and incorporated herein by reference.

The present invention relates to a method for making 9,10-dithiaanthracene-2,3,6,7-tetracarboxylic acid dianhydride, or derivatives, referred to hereinafter as "thianthrene dianhydride" and to polyimides having glass transition temperatures in excess of 400° C.

Prior to the present invention, aromatic polyimides were generally recognized as organic materials having superior solvent resistance and temperature resistance. Aromatic polyimides can generally be made by intercondensing aromatic dianhydrides with aliphatic or aromatic diamines. One technique for improving the glass transition temperature ($T_g$) of aromatic polyimides is by intercondensing aromatic dianhydrides with aromatic diamines. Further improvements can be achieved in aromatic polyimide properties by utilizing a particular dianhydride to provide a polyamic acid which is convertible to a polyimide having higher temperature resistance and solvent resistance upon heating.

The present invention is based on the discovery that aromatic polyimides having glass transition temperatures in excess of 400° C. can be made by intercondensing one or more aromatic diamines, such as methylene dianiline or metaphenylene diamine with thianthrene dianhydride having the formula,

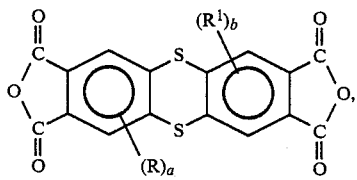

where R, and $R^1$ are selected from the same or different $C_{(1-8)}$ alkyl radicals, $C_{(1-8)}$ alkoxy radicals, and $C_{(6-14)}$ aryl radicals, and a and b are whole numbers equal to 0 or 1.

STATEMENT OF THE INVENTION

There is provided by the present invention, polyimides comprising chemically combined units of the formula,

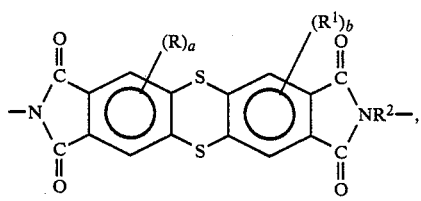

where R and $R^1$ are as previously defined and $R^2$ is a $C_{(6-30)}$ divalent aromatic organic radical.

There is also included by the present invention, a method for making thianthrene dianhydride of formula (1), comprising effecting reaction between an alkali metal sulfide and an N organo-4,5-dihalophthalimide of the formula,

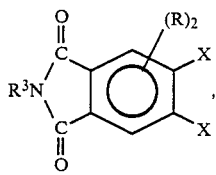

where R and a are as previously defined, $R^3$ is selected from monovalent $C_{(1-14)}$ hydrocarbon radical, or $C_{(1-14)}$ monovalent hydrocarbon radical substituted with radicals inert during halogen displacement, or substitution reactions, to produce the corresponding bisimide of the formula,

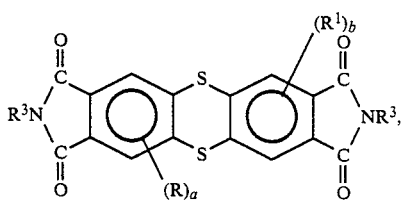

where R, $R^1$, $R^3$, a and b are as previously defined.

Hydrolysis of the thianthrene bisimide of formula (4) in the presence of an aqueous base followed by acidification and ring closure provides the thianthrene dianhydride of formula (1).

Polyimides consisting essentially of chemically combined units of formula (2) can be made by the intercondensing substantially equal molar amounts of thianthrene dianhydride of formula (1) with organic diamine of the formula, $$NH_2R^2NH_2, \qquad (5)$$

where $R^2$ is as previously defined in the presence of an inert organic solvent to produce the corresponding polyamic acid. Polyamic acid solutions having from 5% to 50% by weight of solids, based on the total weight of solution, can be used in combination with fillers, such as carbon fibers, or glass fibers, to produce high temperature composites.

Radicals which are included within R and $R^1$ of formula (1) are for example $C_{(1-8)}$ alkyl radicals, such as methyl, ethyl, propyl, butyl, pentyl; aryl radicals, such as phenyl, xylyl, tolyl, naphthyl and halogenated derivatives thereof, for example or chlorophenyl, bromonaphthyl, etc. Radicals which are included within $R^2$ of formulas (2) and (5) are for example phenylene, phenyleneoxyphenylene and divalent radicals of the formula,

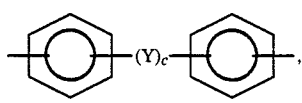

where Y is a member selected from —S—,

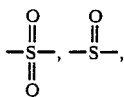

$-C_x(H_2)_x$, x is an integer having a value of 1 to 5 inclusive, and c is a whole number equal to 0 or 1.

Radicals which are included within $R^3$ of formula (3) are for example $C_{(1-8)}$ alkyl radicals such as methyl, ethyl, propyl and $C_{(6-14)}$ aryl radicals such as phenyl, napthyl, anthryl and such aryl radicals substituted with radicals neutral during intercondensation, displacement or substitution reactons.

Some of the aryl diamines which are included within formula (5) are, for example,

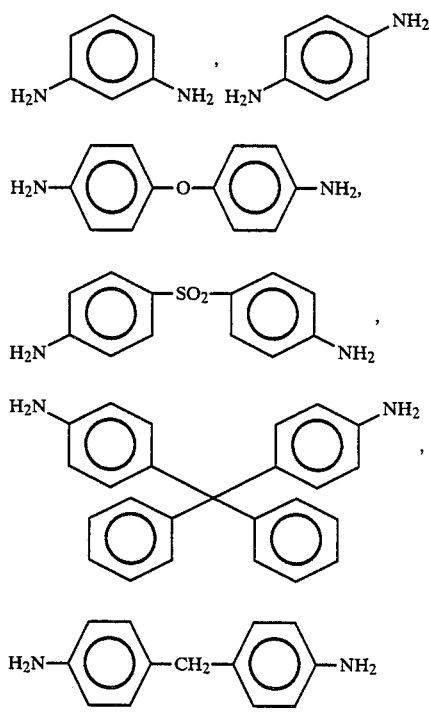

In the practice of one form of the invention substantially equal molar amounts of the dihaloimide of formula (3), and an alkali metal sulfide, such as sodium sulfide or potassium sulfide is contacted in the presence of an inert organic solvent under substantially anhydrous conditions at a temperature in a range of from 50° C. to 200° C. Recovery of the bisimide can be readily achieved by standard procedure such as filtration, washing with organic solvent and drying.

Hydrolysis of the bisimide can be achieved by agitating the bisimide in the presence of an aqueous base such as an aqueous solution of an alkali metal hydroxide, for example potassium hydroxide along with heating the mixture to reflux. Separation of water and organic amine can be readily effected and the process continued, with the addition of water until the distillate is substantially neutral. The resulting tetraacid can be separated by standard means followed by dehydration and recrystallization.

The intercondensation of thianthrene dianhydride and organic diamine to a polyamic acid can be achieved by employing substantially equal molar amounts of the reactants in the presence of a suitable inert organic solvent preferably, an aprotic dipolar organic solvent can be used under substantially anhydrous conditions at ambient temperatures. Suitable organic solvents are, for example, N,N-dimethylformamide, N,N-dimethylacetamide, and N-methyl-2-pyrrolidone.

If desired, thianthrene dianhydride of formula (1) can be blended with up to about 2 to 75 mole percent of other dianhydrides, such as phthalic anhydride, pyromellitic dianhydride, benzophenone dianhydride, oxydiphthalic acid anhydride, sulfur diphthalic acid anhydride, hydroquinone dianhydride and bisphenol A dianhydride.

The resulting polyamic acid can be applied onto a substrate, or mixed with an appropriate reinforcing filler, such as a carbon fiber, or glass fiber. There can be utilized from about 50 to 500 parts of fiber, per 100 parts of polyamic acid. The polyamic acid can be heated under a slight vacuum under nitrogen at a temperature in the range of from 30° to 100° c. and thereafter imidized by programmed heating at temperatures in the range of between 100° C. to 400° C.

In order that those skilled in the art will be better able to practice the present invention, the following examples are given by way of illustration and not by way of limitation. All parts are by weight.

EXAMPLE 1

A mixture of 6.006 g (77 mmol) of anhydrous sodium sulfide, 17.57 g (76.39 mmol) of N-methyl-4,5-dichlorophthalimide and 300 ml of dry N,N-dimethylacetamide was heated to 160° C. for a two hour period with stirring. A bright yellow solid separated from the reaction mixture. After the mixture had cooled to room temperature, it was filtered and a crude solid was recovered. The solid was washed with ether and dried overnight in a vacuum oven. The light yellow solid weighed 12 g or a yield of 82.2%. It had a melting point of 392.7° C. Based on method of preparation, the solid was N,N'-dimethylthianthrene-2,3,6,7-tetracarboxylic acid bisimide. The identity of the compound was further confirmed by field desorption mass spectrometry which exhibited one signal at m/c 382 corresponding to the molecular ion of the substance.

A mixture of 31 g (81 mmol) of the above thianthrene bisimide, 32.3 g (486 mmol) of KOH pellets (85%) and 200 ml of water was heated to reflux while stirring. Water and methylamine were continuously distilled from the mixture and replaced with fresh water. There was obtained 14.42 g of a 50% yield of thianthrene dianhydride after the corresponding tetraacid was vacuum oven dried for a period of 16 hours. The dianhydride was obtained by recrystallization of the resulting solid from orthodichlorobenzene containing a trace of acetic anhydride. The resulting dianhydride had a melting point (DSC) of 349° C., mass spectrum (high resolution EI) calcd for $C_{16}H_4O_6S_2$ to 355.9449; Found 355.9441.

EXAMPLE 2

A mixture of 400 mg (2.0 mmol) of 4,4'-diaminodiphenylether, 712 mg (2.0 mmol) of thianthrene dianhydride and 6.0 ml of dry DMAC was stirred at ambient temperature for one hour. It was then spread on a dry glass plate. The sample was heated overnight under a slight vacuum with an nitrogen bleed at 70°-75° C. The resulting amic acid film was then imidized by a programmed heating as follows: 100° C., 1 hour; 200° C., 1 hour; 300° C., 30 minutes; 400° C., 15 minutes; 450° C., 15 minutes. The resulting film was dark amber and somewhat brittle. Yield 815 mg (78.4%); $T_g$ (TMA)=412° C. Based on method of preparation the product was a polyimide consisting essentially of chemically combined units of the formula,

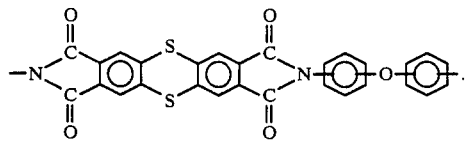

The above procedure was repeated except in place of the 4,4'-diaminodiphenylether there was utilized methylenedianiline (MDA), m-phenylenediamine (MPD), p-phenylenediamine (PPD), oxydianiline (ODA) and a mixture of equal molar amounts of MPD and PPD. The $T_g$ of the polyimides which were obtained from the respective aryldiamines are shown as follows,

| Diamine | $T_g$ |
| --- | --- |
| MDA | 395 |
| MPD | 405 |
| PPD | 400 |
| ODA | 412 |
| MPD/PPD(1/1) | 399 |

EXAMPLE 3

A polyimide was prepared in accordance with the method of Example 2, utilizing substantially equal molar amounts of p-phenylenediamine and thianthrene dianhydride. A film of the polyimide was cut into strips and weighed in glass vials. The weights of the polyimide strip ranged from 0.3-0.5 gms.

Several commercially available polyimides, such as Kapton ® polyimide, and Upilex ® polyimide also were evaluated following the same procedure. The vials were placed in a hot block maintained at 371±5° C. Sample weights were taken at regular intervals over a 150 hr period. The isothermal weight loss of the samples over a 100 hr and 150 hr period of 371° C., indicating "thermal oxidative stability" is shown as follows:

| Polyimide | $T_g$ | 100 hrs | 150 hrs |
| --- | --- | --- | --- |
| Kapton ® | 399 | 15.3 | 23 |
| Upilex ® | 283 | 5 | 16 |
| NR-150 | 367 | 3.9 | 6.1 |
| Ultem ® | 215 | 3.8 | 4.9 |
| Thianthrene | 400 | 2.2 | 2.6 |

The above results show that thianthrene polyimide is more oxidatively stable than Kapton ® polyimide made from pyromellitic acid dianhydride. Upilex ®, made from biphenylene dianhydride, NR-150, and Ultem ® polyetherimide made from bisphenol-A dianhydride.

EXAMPLE 4

A solution was stirred for 1 hour at 50° C. under nitrogen consisting of 1 gram of thianthrene dianhydride, 1 gram of 4,4'-bis(phthalic anhydride)oxide, 0.6526 grams of paraphenylenediamine and 16 ml. of N,N-dimethylacetamide. A film from this solution was cast upon a dry Pyrex plate. The plate and the film were heated in a vacuum oven for about 12 hours using a slow nitrogen bleed at a temperature of up to about 70° C. The film was then gradually heated at 100° C. for 1 hour, 180° C. for 1 hour, 250° C. for 20 minutes, 300° C. for 20 minutes, 350° C. for 20 minutes and 400° C. for 20 minutes. The resulting film was amber in color and it had a $T_g$ as determined by TMA of 396° C.

EXAMPLE 5

A solution of 1.000 grams of thianthrene dianhydride, 1.000 grams of bisphenol dianhydride, 0.5298 gram of phenylenediamine and 12 ml. N,N-dimethylacetamide was stirred for 2 hours while it was slightly warmed. The thickened mixture was then poured onto a Pyrex plate and heated in accordance with the procedure of Example 4. The $T_g$ of the resulting film was found to be 379° C. as determined by TMA.

EXAMPLE 6

There was added with stirring 13 ml of dry N,N-dimethylacetamide to a mixture under a nitrogen atmosphere consisting of 1.000 gm of thianthrene dianhydride, 1.000 gm of 4,4'-bis(phthalic anhydride)oxide, and 0.6526 gm of p-phenylenediamine. An additional 3 ml of N,N-dimethylacetamide was then added. The pale yellow solution thickened after stirring for one hour at 50° C. A film from this solution was cast upon a dry Pyrex plate. The plate and film were heated in a vacuum oven overnight using a slight vacuum, slow nitrogen bleed, and a temperature no greater than 70° C. After about 12 hours, imidization was completed by gradual heating as follows: 100° C. for one hour, 180° C. for one hour, 250 C. for 20 minutes, 300° C. for 20 minutes, 350° C. for 20 minutes, and, finally, 400° C. for 20 minutes. The film was amber in color. $T_g$, as determined by TMA, was 396° C. Based on method of preparation, there was obtained a polyimide copolymer having chemically combined thianthrene bismide units and bisphthalicimide units.

EXAMPLE 7

In accordance with the procedure of Example 6, additional polyimide copolymers were made by effecting intercondensation of a mixture of thianthrene dianhydride with other aromatic dianhydrides with an appropriate diamine utilizing dipolar aprotic solvents. The following table shows the $T_g$s obtained from several copolymers resulting from the intercondensation of paraphenylenediamine with mixtures of thianthrene dianhydride and other aromatic dianhydrides, where PA is phthalic anhydride, ODAN is 4,4'-oxyphthalic anhydride, SDA is 4,4'-sulfur bisphthalic anhydride, and HQDA is hydroquinone dianhydride.

| Anhydride | $T_g$ (°C.) |
| --- | --- |
| 1 | 392 |
| 1 + 2% PA | 399 |
| 1/ODAN$^a$ (3/1) | 386 |
| 1/ODAN (1/3) | 307 |
| 1/SDA (1/1) | 396 |
| 1/HQDA (1/1) | 355 |

EXAMPLE 8

In accordance with the procedure of Example 6, there was added 12 ml of dry N,N-dimethylacetamide to 1.000 gm of thianthrene dianhydride, 1.000 gm of biphenol dianhydride, and 0.5298 gm of p-phenylendiamine. The mixture washed warm to form a solution.

After two hours, the solution thickened. A film was poured onto a Pyrex plate and the imidization was performed, as above, using a temperature gradient. The $T_g$, as determined by TMA, was 379° C.

Although the above results are directed to only a few of the very many variables which can be used in the practice of the present invention, it should be understood that the present invention is directed to a much broad variety of polyimides and methods for making them as shown in the description preceding these examples.

What is claimed and sought to be protected by Letters Patent of the United States is as follows:

1. A method for making thianthrene dianhydride which comprises,
   (1) effecting reaction between substantially equal moles of an alkali metal sulfide and an N-organo-4,5,-dihalophthalimide of the formula,

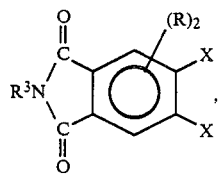

to produce a bisimide;
   (2) hydrolyzing the bisimide in aqueous base; and
   (3) dehydrating the resulting tetra acid;
where R is selected from $C_{(1-8)}$ alkyl radicals, $C_{(1-8)}$ alkoxy radicals and $C_{(6-14)}$ aryl radicals, $R^3$ is selected from monovalent $C_{(1-14)}$ hydrocarbon radicals, or $C_{(1-14)}$ monovalent hydrocarbon radicals substituted with radicals neutral during sulfur and halogen displacement or substitution reactions, and X is a halogen radical.

* * * * *